United States Patent [19]

Cooper et al.

[11] Patent Number: 5,000,049
[45] Date of Patent: Mar. 19, 1991

[54] PRESSURE GAUGE FOR MEDICAL APPLICATIONS

[76] Inventors: Robert P. Cooper, 19332 Via de la Cielo, Yorba Linda, Calif. 92686; Said S. Hilal, 25291 Spindlewood St., Laguna Niguel, Calif. 92677

[21] Appl. No.: 227,580

[22] Filed: Aug. 2, 1988

[51] Int. Cl.⁵ .................... A61B 5/00; G01L 7/08
[52] U.S. Cl. ........................... 73/730; 73/747; 128/748
[58] Field of Search ........... 73/730, 741, 756, 732; 128/673, 675, 748

[56] References Cited

U.S. PATENT DOCUMENTS

| | | | |
|---|---|---|---|
| 3,240,207 | 3/1966 | Barker et al. | 73/730 |
| 3,418,853 | 12/1968 | Curtis | 128/675 |
| 4,610,256 | 9/1986 | Wallace | 128/673 |

*Primary Examiner*—Donald O. Woodiel
*Attorney, Agent, or Firm*—Richard L. Myers

[57] ABSTRACT

An apparatus for measuring fluid pressure in a passage or tube for use with medical apparatus such as balloon catheters. A diaphragm gauge is provided and includes a case which houses a first diaphragm, a translation mechanism connected to the first diaphragm and a pointer attached to the translation mechanism for providing readouts of fluid pressure. The diaphragm is coupled to a fluid passage, such that changes in fluid pressure cause the diaphragm to activate the translation mechanism, thus providing readouts by means of the pointer. A second diaphragm is provided for sealing the fluid passage from the first diaphragm, for preventing transfer of materials between the first diaphragm and the passage. The second diaphragm is of a biocompatible, nonpyrogenic, sterlizable material, such a polyurethane, polyvinylchloride, or polyethylene. Alternatively, a biocompatible, nonpyrogenic coating may be provided on the first diaphragm for sealing it from the fluid passage. In an alternative embodiment, the fluid passage is configured for tightly receiving a catheter, the wall of which contacts the first diaphragm for transmitting pressure due to fluid within the catheter to the first diaphragm. The translation mechanism may be a mechanical lever for converting diaphragm movements to rotational movement of the pointer, or it may be an electronic transducer, in which case the pointer and dial are replaced by an electronically actuable display.

8 Claims, 3 Drawing Sheets

PRESSURE GAUGE FOR MEDICAL APPLICATIONS

TECHNICAL FIELD

The invention relates to pressure gauge mechanisms for use in medical applications.

BACKGROUND ART

Injection of solutions into balloon catheters to inflate the balloons is conducted hundreds of thousands of times every year. This invention addresses the need to monitor inflation pressures in angioplasty balloon catheters. In angioplasty, a catheter is maneuvered into the obstructed blood vessel or any other obstructed tract and a balloon at the tip of the catheter is inflated to compress plaque or alleviate strictures. During such procedures, physicians require the ability to monitor pressure applied within the balloon for safety and efficacy related reasons.

Angioplasty, or balloon dilatation, was introduced by the late Dr. A. Gruntzig in the early seventies. The approach utilized the concept of a dilatation catheter. A catheter is a hollow polymeric (i.e., polyurethane, polyvinylchloride, polyethylene, etc.) tube, sometimes designed with multiple lumens to facilitate infusions or pressure monitoring, or with braided wire support in the catheter wall to improve its torque control or "steerability." A dilatation catheter is a specifically designed catheter with a high strength balloon at its tip.

The most common application of angioplasty is in the coronaries. The percutaneous transluminal coronary angioplasty (PTCA) procedure involves: (a) an introducer sheath; (b) a guiding catheter; (c) a balloon catheter; (d) a steerable guide wire; (e) radiologic equipment; (f) monitoring equipment; (g) manifolds, valves, adaptors and tubing assembled by the operator to form an infusion system; and (h) an inflation device and pressure gauge to inflate and deflate the balloon to desired pressures to affect dilatation.

Three key requirements that hold throughout such procedures are: (i) the biocompatibility and non-pyrogenecity of all components that can possibly come in contact with the patient's tissue or blood, including such components that may come in contact with solutions that eventually may contact body tissue or blood; (ii) the total freedom of the whole system from any air bubbles which, if somehow allowed within the body, can cause embolisms with injurious or fatal consequences; and (iii) the ability to monitor inflation pressures accurately, including negative pressure generated by partial vacuum in the fluid lines.

So far, the above-mentioned medical requirements have been observed steadfastly, except in the case of pressure gauges used in such procedures. Such mechanisms have not been made biocompatible, nonpyrogenic or safe from gas bubble entrapments to the extent necessary by the nature of the application. Generally speaking, there are three widely used types of mechanical pressure gauge mechanisms, as discussed below.

A. C-tube Gauge

A common type of gauge mechanism is the standard C-tube pressure gauge 5, depicted in the exploded view of FIG. 1. The gauge 5 includes a tube 10, which is flattened to a predetermined extent and then bent into a "C" shape. An inlet end 20 of the tube is connected to an inlet 30 of the pressure gauge 5, and the other end 35 is connected via a lever or other conventional translation mechanism 40 to a pointer mechanism 50. When the inlet 30 is hooked up to a pressurized fluid, the pressure of the fluid is transmitted to the C-tube 10, and the C-tube straightens out to a certain extent (proportionately to the fluid pressure), causing the pointer 50 (by means of the mechanism 40) to rotate against a dial background 60. A case 70 is provided to house the gauge mechanism. The same concept also works in the reverse, i.e., if subjected to external pressure or vacuum, said C-tube will bend accordingly, generating a corresponding reading on the pointer 50 relative to the dial 60. An example of such a gauge is the SEA-DIVE gauge available from U.S. Divers of Santa Ana, Calif.

The most significant advantage of this type of mechanism is the low cost associated with the manufacturing of the device. This type of mechanism lends itself to mass production and automation.

The disadvantages are numerous. This type of mechanism has a high internal volume compared to other mechanisms. In case of failure, therefore, the explosive mode of the mechanism will reflect a much higher energy, especially if the fluid is compressible or if air is entrapped within the C-tube. Entrapment of air is a particular problem, due to the dead-end shape of the C-tube. This aspect is of especial concern in medical applications where, as mentioned before, air bubbles cannot be tolerated.

Another serious disadvantage is the infeasibility of cleaning the inside of a C-tube mechanism to the extent necessary to prevent pyrogenic reaction in the body. The dead-end design of the C-tube makes adequate cleaning very expensive, yet still unreliable.

Another disadvantage of C-tube mechanisms relates to the soldering requirement during the manufacturing process. Soldering is an operation which typically yields connections of varying strength and overall quality, often leading to leakages. Also, the process of soldering leaves debris and loose bits of solder which can get washed out during use of the device. This is a problem, especially because most solder is chemically active with radiopaque dyes or other medical solutions.

These disadvantages make the C-tube mechanism less than adequate for medical applications. One way to minimize such disadvantages has been to manufacture the C-tube from fairly inactive material, and to utilize very fine filters (such as forty-micron filters), to prevent the washing out of particles during use. However, this approach does not reduce the volumetric characteristics of the gauge, nor does it address the issue of entrapped air. In addition, it adds considerably to the expense and inconvenience of manufacture and use of the gauge.

B. Spiral or Helical Coil Gauge

A conventional spiral coil gauge 80 is depicted in FIG. 2, and includes a small diameter coiled tube 90, flattened to a desired extent and then coiled in a concentric, essentially circular fashion. The innermost end 100 is connected to pointer 120 while the outer end 110 is connected to fluid source under pressure via an inlet 115. When the spiral tube or coil 90 is subjected to pressure, the coil unwinds to an extent proportionate to the pressure, thus forcing the pointer 120 to rotate relative to a dial 130. A case 140 houses the mechanism, and is preferably attached to the inlet 115. An example of this type of gauge is the PRO-DIVE I gauge available from U.S. Divers.

Advantages of a gauge such as the spiral coil gauge 80 are low internal volume and high resistance to shock. The device is best suited for use in high pressure situations, and especially those involving highly compressible fluids.

The disadvantages are high cost, small sweep angle for the pointer 120, minimal usefulness with highly viscous fluids, and air entrapment within the spiral coil. The spiral coil also has the same disadvantage of C-tube mechanisms regarding cleanliness, pyrogenecity and soldering debris.

Another big disadvantage is low accuracy at the low end of the scale, i.e. at low pressures.

C. The Diaphragm Gauge

A conventional diaphragm gauge 150 is shown in FIG. 3, and includes a case 160 having a diaphragm 170 mounted thereon, and a translation mechanism 180. Connected to the mechanism 180 is a pointer 190 which is rotatable relative to a dial face 200. As pressurized fluid contacts the diaphragm 170, the pressure is transmitted to the mechanism 180, which is of conventional design and may include a mechanical arm, a sealed volume of a relatively incompressible fluid, or other mechanism for translating movement of the diaphragm under pressure into a rotational movement for the gauge pointer 190.

One such translational mechanism (in the DIVEMASTER gauge manufactured by U.S. Divers) relies on an evacuated C-tube which bends more acutely under increasing external pressure.

The key advantage of the diaphragm gauge is the accuracy and large angle of sweep for the pointer. Another key advantage for the non-fluid filled diaphragm gauge is the low cost of manufacture.

However, none of the above mechanisms addresses the full needs of the medical applications at hand. The C-tube gauges expose the medical grade fluids to materials that do not pass the qualification for biocompatibility, cleanliness or pyrogenecity. The same is true of the spiral coil gauge, which has the added disadvantage of low accuracy in the ranges pertinent to medical applications. The diaphragm gauge has the same generic shortfall except that the fluid can possibly be isolated from the mechanism itself, though not the sensing diaphragm. Additionally, none of these gauges addresses the real requirement of a fluid path that is air-bubble free. To enhance the present state of the art, the improved pressure gauge must not only be biocompatible and nonpyrogenic, but also of such a configuration as to prevent the highly undesirable entrapment of air, especially since entrapped air bubbles in a dead-end tube, under repeatedly increasing and decreasing pressures, have a very high likelihood of dissolving in the fluid medium. Also, when negative pressure, i.e., suction, is applied to the fluid path, there is a high likelihood that entrapped air will be sucked out of the gauge and into the fluid medium.

The shortcomings and limitations of existing pressure gauge devices as they pertain to medical applications are the subject of the invention described here.

It is therefore an object of the present invention to provide a pressure gauge for medical applications, whose fluid path is biocompatible, sterilizable and nonpyrogenic, without reverting to highly expensive means that are unsuitable for the single-use applications in the medical field.

Another objective of the invention is to provide a pressure gauge for medical applications whose fluid path avoids the entrapment of air bubbles.

Another objective of the invention is to provide a pressure gauge for medical applications which has the capability of accurately indicating pressures below one atmosphere (absolute pressure).

Another objective of the invention is to provide said gauge at an economic price compatible with the single-use nature of the product in medical applications.

Another objective of the invention is to accomplish all the aforementioned while keeping the device compact and easy to use.

SUMMARY OF THE INVENTION

A biocompatible, nonpyrogenic diaphragm-type pressure gauge having a first diaphragm for responding to pressure and fluid path that permits transfer of pressure from the fluid path to the diaphragm without requiring the fluid to leave the fluid path or enter the pressure mechanism. The assembly is constructed from biocompatible, nonpyrogenic and sterilizable material. A housing for the fluid path is of a geometric shape and construction as to allow the subject fluid to flow from entrance to exit without entrapping air bubbles against a closed or dead-ended path or tube. A second diaphragm may be disposed adjacent the first diaphragm for transmitting pressure changes thereto without allowing the passage of materials between the diaphragms. Alternatively, the first diaphragm may be sealed with a biocompatible, nonpyrogenic material. In an alternative embodiment, the fluid path may be adapted for tightly receiving a catheter, and the catheter wall is disposed against the first diaphragm, such that fluid pressure changes are sensed by the diaphragm without contact of the first diaphragm with the fluid.

DESCRIPTION OF THE PREFERRED EMBODIMENT

Figure 1:
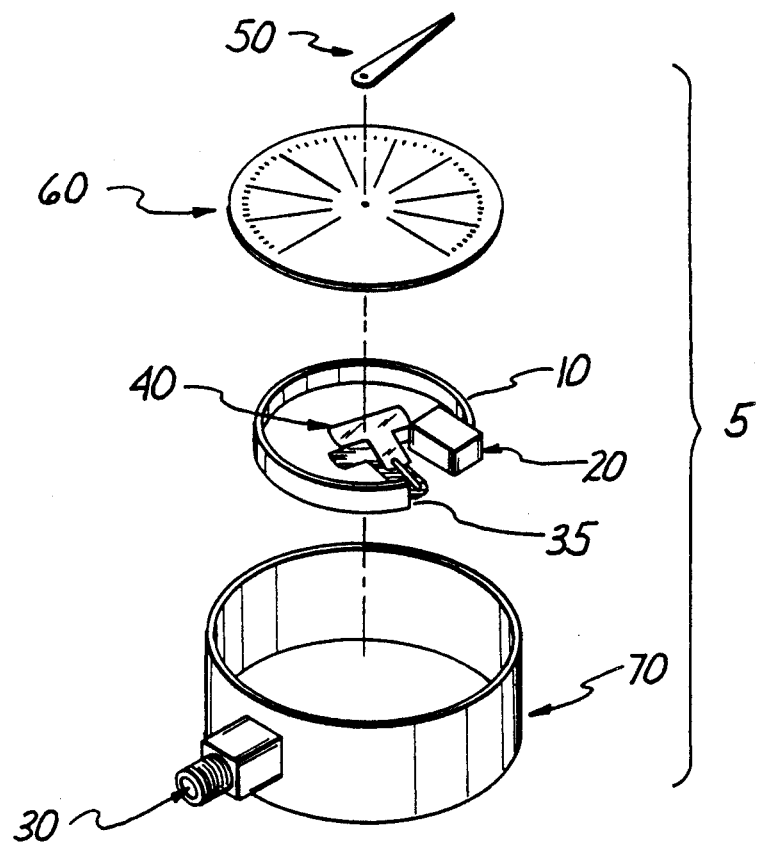
FIG. 1 is an exploded view of a C-tube type of pressure gauge.
Figure 3:
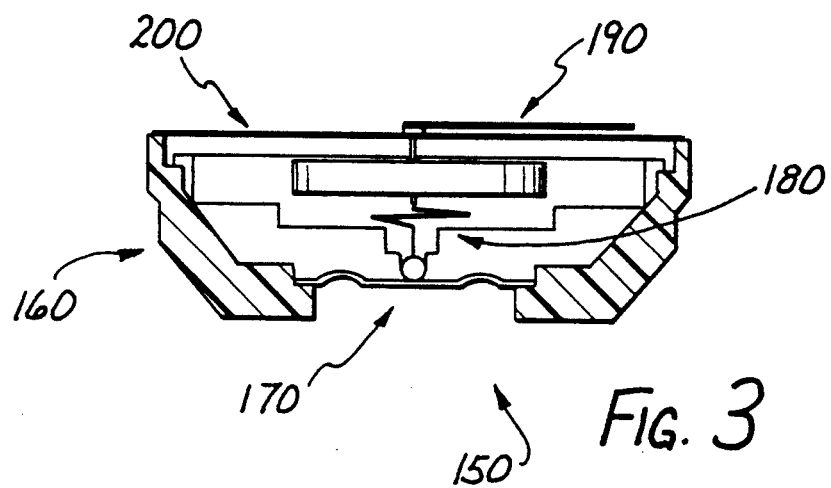
FIG. 3 is a cross-sectional view of a diaphragm type of pressure gauge.
Figure 2:
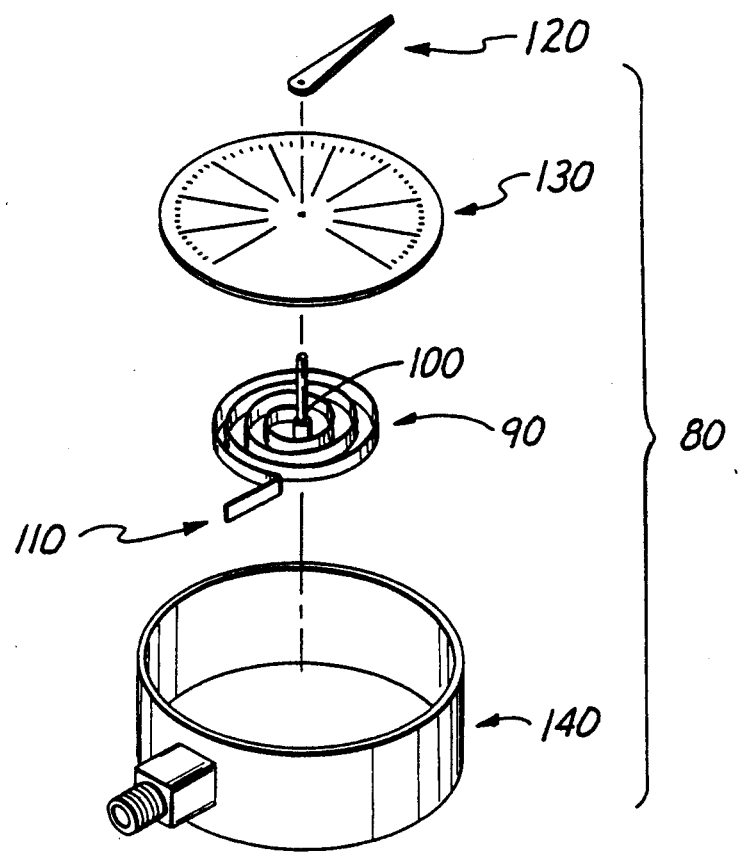
FIG. 2 is an exploded view of a spiral coil type of pressure gauge.
Figure 4:
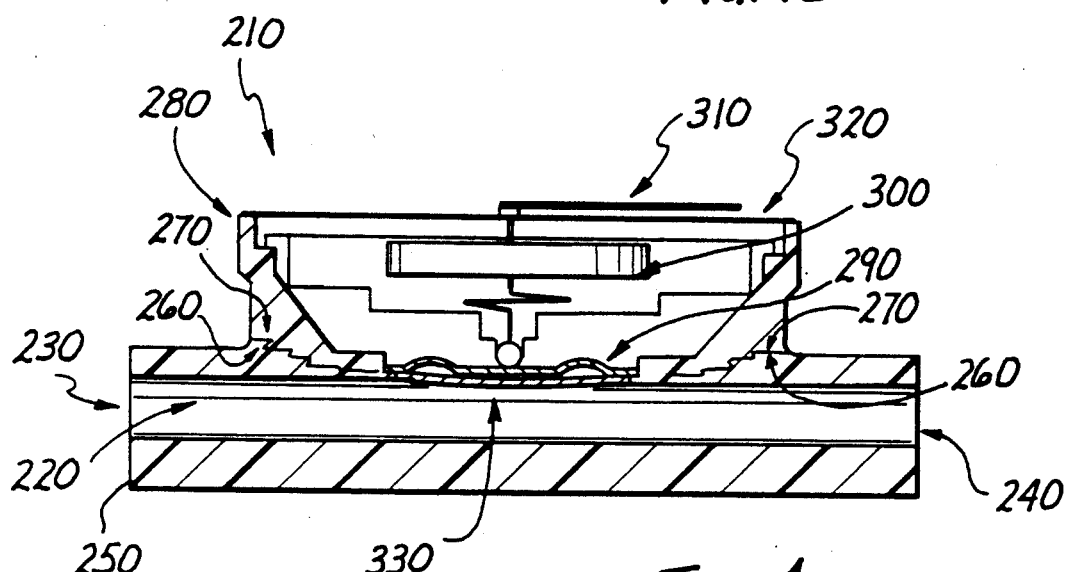
FIG. 4 is a cross-sectional view of the preferred embodiment of the present invention.

As shown in FIG. 4, the preferred embodiment of the present invention comprises a gauge 210 which is integral with or connected in a sealed fashion to a fluid path 220 having an inlet 230 and an outlet 240. The fluid path 220 is defined by a tube 250, which may include threads 260 which are generally circular for receiving the gauge 210. If threads 260 are utilized, then the gauge 210 is provided with complementary threads 270 at its bottom end.

As with the gauge 150, the gauge 210 includes a case 280 carrying a pressure-sensitive diaphragm 290, and a conventional translation mechanism 300. The diaphragm may be of silicon or some other flexible, responsive material. A pointer 310 is connected to the mechanism 300 in a rotatable fashion relative to a pressure dial 320. A sealing diaphragm 330 is provided between the fluid path 220 and the diaphragm 290.

The tube 250 is intended for use in the injection of solutions into balloon catheters for angioplasty. Therefore, the tube 250 should be of a biocompatible, nonpyrogenic and sterilizable material. Likewise, the sealing diaphragm 330 should be of such a material, such as polyethylene, polyurethane, polyvinylchloride, or the like.

The tube 250 preferably includes appropriate standard medical connectors at the inlet 230 and outlet 240 of the fluid path 220. Such connectors facilitate the attachment of the pressure gauge to the desired set up in the safest, most effective manner.

The diaphragm 330 is preferably seated tightly adjacent the diaphragm 290 so that when fluid under pressure is introduced into the fluid path 220, the diaphragm 330 will flex upwardly from the point of view of FIG. 4, thereby causing the diaphragm 290 also to flex upwardly. This upward deflection is thus transmitted to the mechanism 300, and is translated into a rotational movement of the pointer 310, reflecting the pressure of the fluid present in the path 220.

The invention as shown in FIG. 4 may be constructed by first producing a tube 250 having threads 260 at one side thereof. An aperture is provided essentially at the center of the threads 260, and in the aperture the diaphragm 330 is permanently affixed with a biocompatible adhesive means. Alternatively, the diaphragm 330 may be integral with the tube 250, in which case the diaphragm 330 would be manufactured along with the tube 250.

The diaphragm 330 must be strong enough to withstand the typical pressures of the application for the application of the gauge 210, such as introduction of fluids into a balloon catheter. On the other hand, the diaphragm 330 must be light and flexible enough to respond quickly and in a repeatable fashion to changes in fluid pressure.

An advantage of the configuration shown in FIG. 4 is that, while the gauge 310 is sensitive to relatively low pressures such as those used in medical applications, at the same time the strength and stiffness provided by the double-diaphragm arrangement allow for readings of much higher pressures, such as up to 300 psi. It will be appreciated that the diaphragms 290 and 330 may be manufactured as a unit in the assembly of the gauge 210.

The gauge 210, as mentioned above, is provided with threads 270, which are mated with threads 260 to affix the gauge 210 firmly adjacent the tube 250, seating the diaphragm 290 against the diaphragm 330.

It will be understood from the above that, in the embodiment shown in FIG. 4, fluid may flow through the passage 220 in an unobstructed manner, and at the same time convey the pressure fluid to the diaphragm 330, and thereby to the gauge mechanism 300, without the fluid ever contacting the diaphragm 290 or any other portion of the gauge 210, and without actually leaving the fluid path 220. Thus, the only material other than the tube 250 which is presented to the fluid in the path 220 is the material of the diaphragm 330, and in the present invention it is ensured that this material is biocompatible and nonpyrogenic. A standard diaphragm gauge may be utilized as the gauge 210, so long as it is provided with threads 270, and thus it is unnecessary in this embodiment that the diaphragm 290 be made biocompatible or nonpyrogenic.

The diaphragm 330 is preferably made flush with the inner walls of the tube 250 defining the fluid path 220, eliminating the possibility of any air entrapment in the vicinity of the gauge 210.

Figure 5:
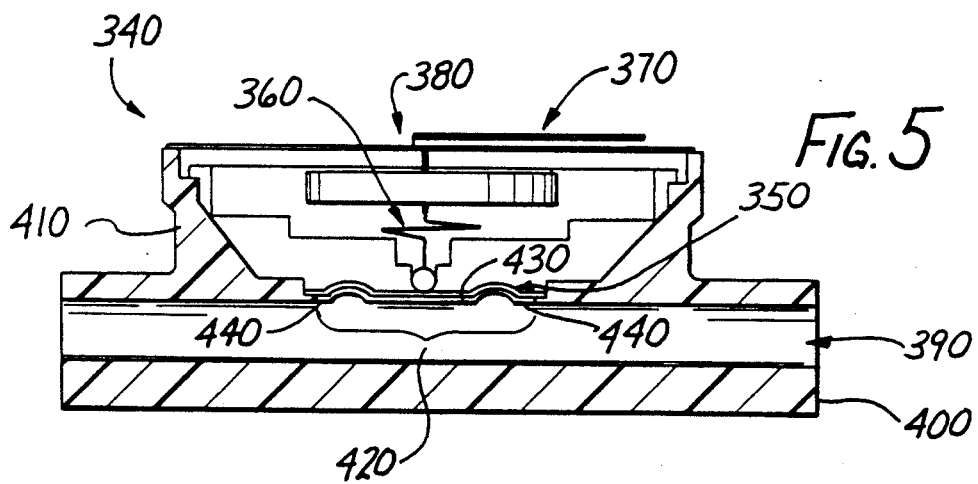
FIG. 5 is a cross-sectional view of an alternative embodiment of the present invention.

In the embodiment of FIG. 5, a fluid pressure gauge 340 is provided, again of the diaphragm pressure gauge type, including a diaphragm 350, a conventional translation mechanism 360, and a pointer 370 attached to the mechanism 360 in a rotatable fashion relative to a dial 380. As in FIG. 4, a fluid path 390 is provided, being defined by a tube 400. In this embodiment, the pressure gauge 340 includes an annular wall 410 which is integral with the tube 400. The gauge 340 is assembled by first mounting the diaphragm 350 at a lateral aperture 420 provided in the tube 400. The diaphragm may be formed from a biocompatible and nonpyrogenic material, or if it is not then a biocompatible, nonpyrogenic coating 430 may be applied. The diaphragm 350 is adhered to the tube 400, such as at an annular flange 440 which is integral with the tube 400 and/or the annular wall 410, and effectively defines the aperture 420. The edges of the diaphragm 350 (or of the coating 430, if such coating is utilized) are preferably flush with the flange 440, to prevent air entrapment.

Figure 6:
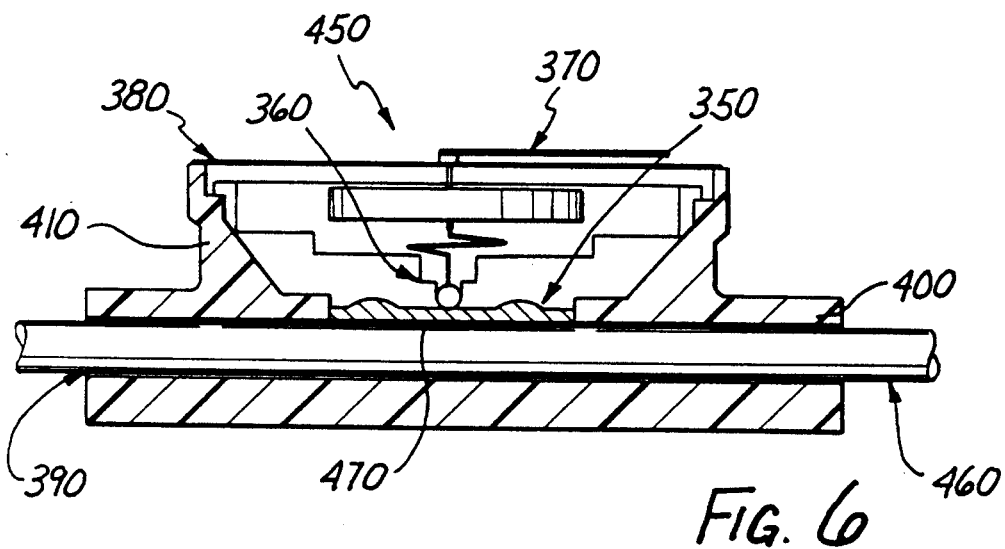
FIG. 6 is a cross-sectional view of another alternative embodiment of the present invention.

Yet another embodiment of the invention is shown in FIG. 6, wherein a diaphragm-type pressure gauge 450 is shown, and is identical in many respects to the embodiment shown in FIG. 5. Thus, the various elements of the embodiment of FIG. 6 are numbered in the same fashion as those of FIG. 5. However, in this embodiment the tube 400 is designed to receive a catheter 460 or another flexible tube where it is desired that fluid under pressure within the tube is isolated from the pressure detecting mechanism. In this embodiment, the coating 430 may be omitted, and the diaphragm 350 is constructed so that it has an inner surface 470 which is substantially flush with the inner wall of the tube 400. Additionally, the fluid path 390 preferably has a diameter which closely conforms to an outside diameter of the catheter 460. In this embodiment, the material of which the catheter 460 is formed acts to translate pressure of fluid within the catheter 460 to the diaphragm 350, thus activating the mechanism 360. It will be appreciated that in this embodiment, fluid travels through the catheter 460 but does not otherwise travel through the fluid path 390. Thus, fluid does not directly contact the tube 400 or the diaphragm 350 in this configuration.

Figure 7:
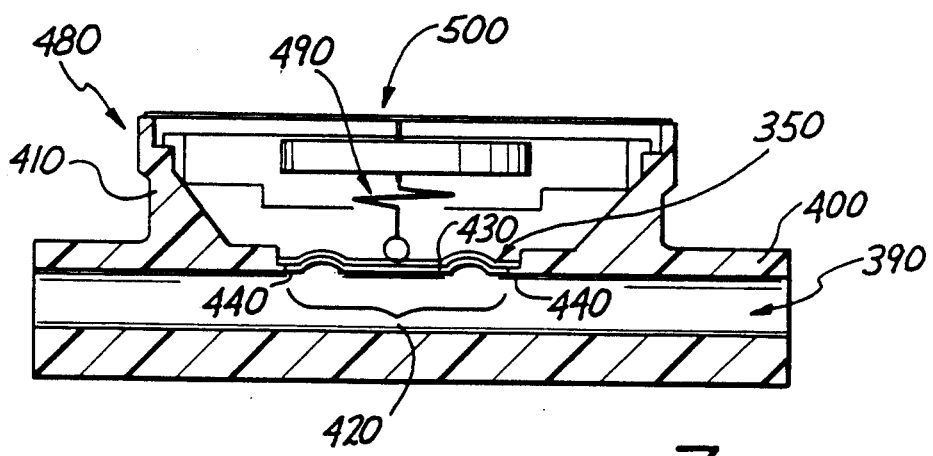
FIG. 7 is a cross-sectional view of another embodiment of the invention.

FIG. 7 shows an alternative embodiment of the invention, which is in some respects similar to the embodiment shown in FIG. 5, and therefore for similar features the same numerals are used. In FIG. 7, a pressure gauge 480 is shown but in place of the mechanical translation mechanism 360 of FIG. 5, an electronic transducer 490 is utilized, providing a read out at display 500. The transducer 490 may comprise a piezoelectric type of pressure sensing mechanism, or may be another conventional electromechanical or electronic sensor. The display 500 may be a digital liquid crystal display, an analog display, or other means of displaying pressure sensed by the electronic transducer 490.

I claim:

1. An apparatus for measuring pressure of a fluid in a catheter, comprising:
   a longitudinal tube having a wall defining a centrally disposed fluid passage for receiving the fluid;

an aperture in said wall disposed laterally with respect to the tube;

a pressure-responsive first diaphragm mounted at said aperture and sealed against said wall;

a pressure indicator carried by said wall for indicating the pressure of the fluid;

means disposed adjacent and in contact with said first diaphragm, and in a lateral position with respect to said tube, and operatively connected to said indicator for translating the pressure of the fluid at said first diaphragm into readings of said indicator; and means for preventing contact of the fluid with, and transmitting pressure of the fluid to, said first diaphragm, comprising a pressure-responsive second diaphragm mounted at said aperture in a sealed fashion and in contact with said first diaphragm, which second diaphragm flexes in response to changes in the pressure of the fluid and transmits said response directly to said first diaphragm.

2. The apparatus of claim 1, further comprising a case for housing said first diaphragm, said indicator and said translating means, said case including first threads, wherein said tube includes second threads for receiving said first threads for mounting said case on said tube.

3. The apparatus of claim 1, wherein said preventing means is disposed flush to said tube.

4. The apparatus of claim 1, wherein:
said translating means comprises an electronic transducer coupled to said diaphragm; and
said indicator comprises a digital display connected to said transducer for displaying values of the pressure.

5. The apparatus of claim 1, wherein: said translating means comprises a diaphragm gauge coupled to said diaphragm for displaying values of the pressure.

6. An apparatus for measuring pressure of a fluid in a catheter, comprising:
a longitudinal tube having a wall defining a centrally disposed fluid passage for receiving the fluid;
an aperture in said wall disposed laterally with respect to the tube;
a pressure-responsive diaphragm mounted at said aperture and sealed against said wall;
a pressure indicator carried by said wall for indicating the pressure of the fluid;
means disposed adjacent and in contact with said diaphragm, and in a lateral position with respect to said tube, and operatively connected to said indicator for translating the pressure of the fluid at said diaphragm into readings of said indicator; and
means for preventing contact of the fluid with said diaphragm while allowing flexing of said diaphragm in response to changes in the pressure of the fluid;
wherein said preventing means comprises a biocompatible, nonpyrogenic coating on said diaphragm.

7. An apparatus for measuring pressure of a fluid in a catheter having flexible walls, comprising:
a longitudinal tube having a wall defining a centrally disposed passage for receiving the catheter;
an aperture in said wall disposed laterally with respect to the tube;
a pressure-responsive diaphragm mounted at said aperture;
a pressure indicator carried by said wall for indicating the pressure of the fluid; and
means disposed adjacent and in contact with said diaphragm, and in a lateral position with respect to said tube, and operatively connected to said indicator for translating the pressure of the fluid at said diaphragm into readings of said indicator;
wherein said tube is adapted for receiving the catheter in a tight-fitting manner such that changes in the pressure of the fluid are transmitted by the catheter walls to said diaphragm, for preventing contact of the fluid with said diaphragm while allowing flexing of said diaphragm in response to changes in the pressure of the fluid.

8. The apparatus of claim 7, wherein said diaphragm includes an inner surface which is flush with an inner surface of said passage.

* * * * *